US011574402B2

(12) United States Patent
Nakamura et al.

(10) Patent No.: US 11,574,402 B2
(45) Date of Patent: Feb. 7, 2023

(54) INSPECTION INFORMATION DISPLAY DEVICE, METHOD, AND PROGRAM

(71) Applicant: FUJIFILM Corporation, Tokyo (JP)

(72) Inventors: Keigo Nakamura, Tokyo (JP); Noriaki Ida, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 130 days.

(21) Appl. No.: 16/860,047

(22) Filed: Apr. 27, 2020

(65) Prior Publication Data

US 2020/0258226 A1 Aug. 13, 2020

Related U.S. Application Data

(63) Continuation of application No. PCT/JP2018/041962, filed on Nov. 13, 2018.

(30) Foreign Application Priority Data

Nov. 21, 2017 (JP) .............................. JP2017-223629

(51) Int. Cl.
*G06T 7/00* (2017.01)
*G16H 50/20* (2018.01)
(Continued)

(52) U.S. Cl.
CPC .............. *G06T 7/0012* (2013.01); *G06N 3/08* (2013.01); *G16H 30/40* (2018.01); *G16H 50/20* (2018.01); *G06T 2207/10072* (2013.01)

(58) Field of Classification Search
CPC ........ G06T 7/0012; G06T 2207/10072; G16H 50/20; G16H 30/20; G16H 30/40;
(Continued)

(56) References Cited

U.S. PATENT DOCUMENTS 5,970,466 A * 10/1999 Detjen ............... G06Q 10/1095
705/2
8,510,126 B2 8/2013 Martin et al.
(Continued)

FOREIGN PATENT DOCUMENTS

| JP | 2001345961 | 12/2001 |
|----|------------|---------|
| JP | 2005301434 | 10/2005 |

(Continued)

OTHER PUBLICATIONS

"International Search Report (Form PCT/ISA/210) of PCT/JP2018/041962," dated Feb. 12, 2019, with English translation thereof, pp. 1-5.
(Continued)

*Primary Examiner* — Vu Le
*Assistant Examiner* — Julius Chai
(74) *Attorney, Agent, or Firm* — JCIPRNET

(57) ABSTRACT

In inspection information display device, method, and program includes a display controller displays data related to a patient, for example, an analysis result obtained by analyzing a medical image and inspection information related to the data on a display, a decision unit decides at least one of a necessary inspection or a necessary treatment for confirming the analysis result, a resource information acquisition unit acquires resource availability information for executing at least one of the necessary inspection or the necessary treatment for confirming the analysis result, and a display controller 31 further displays the resource availability information on the display.

7 Claims, 9 Drawing Sheets

(51) Int. Cl.
  *G16H 30/40* (2018.01)
  *G06N 3/08* (2006.01)

(58) Field of Classification Search
  CPC ........ G16H 10/60; G16H 40/20; G16H 40/67; G06N 3/08
  See application file for complete search history.

(56) References Cited

U.S. PATENT DOCUMENTS

| | | | |
|---|---|---|---|
| 2005/0228697 A1 | 10/2005 | Funahashi | |
| 2007/0021677 A1* | 1/2007 | Markel | A61B 5/0006 600/509 |
| 2008/0312959 A1* | 12/2008 | Rose | G16H 10/60 705/2 |
| 2009/0164236 A1* | 6/2009 | Gounares | G16H 40/20 705/2 |
| 2009/0216556 A1* | 8/2009 | Martin | G16H 40/63 705/3 |
| 2011/0071850 A1* | 3/2011 | Nuthi | G16H 40/20 705/3 |
| 2012/0016691 A1* | 1/2012 | Sievenpiper | G16H 40/20 705/2 |
| 2012/0116180 A1* | 5/2012 | Rothman | G16H 50/70 600/300 |
| 2015/0294071 A1* | 10/2015 | Machtelinck | G06Q 10/109 705/2 |
| 2017/0357946 A1* | 12/2017 | Zhu | G06Q 10/1095 |
| 2018/0190384 A1* | 7/2018 | Shohat | G16B 20/00 |
| 2019/0035501 A1* | 1/2019 | Zhang | G16H 40/20 |
| 2019/0380782 A1* | 12/2019 | McAfee | A61F 2/4455 |
| 2020/0135330 A1* | 4/2020 | Sugie | G06V 10/25 |

FOREIGN PATENT DOCUMENTS

| | | |
|---|---|---|
| JP | 2007094513 | 4/2007 |
| JP | 2009219867 | 10/2009 |
| JP | 2014153920 | 8/2014 |
| JP | 2016099724 | 5/2016 |
| JP | 2016136323 | 7/2016 |

OTHER PUBLICATIONS

"Written Opinion of the International Searching Authority (Form PCT/ISA/237) of PCT/JP2018/041962," dated Feb. 12, 2019, with English translation thereof, pp. 1-16.

"Office Action of Japan Counterpart Application" with English translation thereof, dated May 18, 2021, p. 1-p. 10.

* cited by examiner

FIG. 2

| RESOURCE | 11/21 00:00 3 6 9 12:00 15 18 21 | 11/22 00:00 3 |
|---|---|---|
| FIRST OPERATING ROOM | ⟵⟶ (9-15) | |
| SECOND OPERATING ROOM | ⟵⟶ (12-15) ⟵⟶ (17-19) | |
| THIRD OPERATING ROOM | ⟵⟶ (14-16) | |
| FIRST INSPECTION ROOM | ⟵⟶ (9-12) ⟵⟶ (13-15) | |
| SECOND INSPECTION ROOM | | |
| FIRST TREATMENT ROOM | ⟵⟶ (9-13) | |
| SECOND TREATMENT ROOM | ⟵⟶ (9-13) | |
| DOCTOR A | ⟵⟶ (10-12) | |
| DOCTOR B | ⟵⟶ (12-16) | |
| NURSE A | ⟵⟶ (10-12) | |
| NURSE B | ⟵⟶ (10-13) | |
| CT | ⟵⟶ ⟵⟶ ⟵⟶ | |
| MRI | ⟵⟶ ⟵⟶ ⟵⟶ | |

DB1

| PORTION | SYMPTOM | INSPECTION AND TREATMENT | |
|---|---|---|---|
| BRAIN | BLEEDING | CT IMAGING, MRI IMAGING, MEDICATION, SURGERY | DB2 |
| | INFARCTION | CT IMAGING, MRI IMAGING, MEDICATION, SURGERY | |
| HEART | CARDIAC INFARCTION | CONTRAST CT IMAGING, MEDICATION, SURGERY | |
| | VENTRICULAR FIBRILLATION | CT IMAGING, MEDICATION, SURGERY | |
| | | | |

FIG. 8

| BLEEDING PORTION | PUTAMINAL HEMORRHAGE | | |
|---|---|---|---|
| | C | B | A |
| SUBCORTICAL HEMORRHAGE | BLEEDING VOLUME: 16 ml OR MORE | BLEEDING VOLUME: 31 ml OR MORE | BLEEDING VOLUME: 50 ml OR MORE |
| CEREBELLAR HEMORRHAGE | BLEEDING VOLUME: 15 ml OR MORE | BLEEDING VOLUME: 30 ml OR MORE | BLEEDING VOLUME: 45 ml OR MORE |
| DEGREE OF URGENCY | BLEEDING VOLUME: 7 ml OR MORE | BLEEDING VOLUME: 14 ml OR MORE | BLEEDING VOLUME: 20 ml OR MORE |

DB3

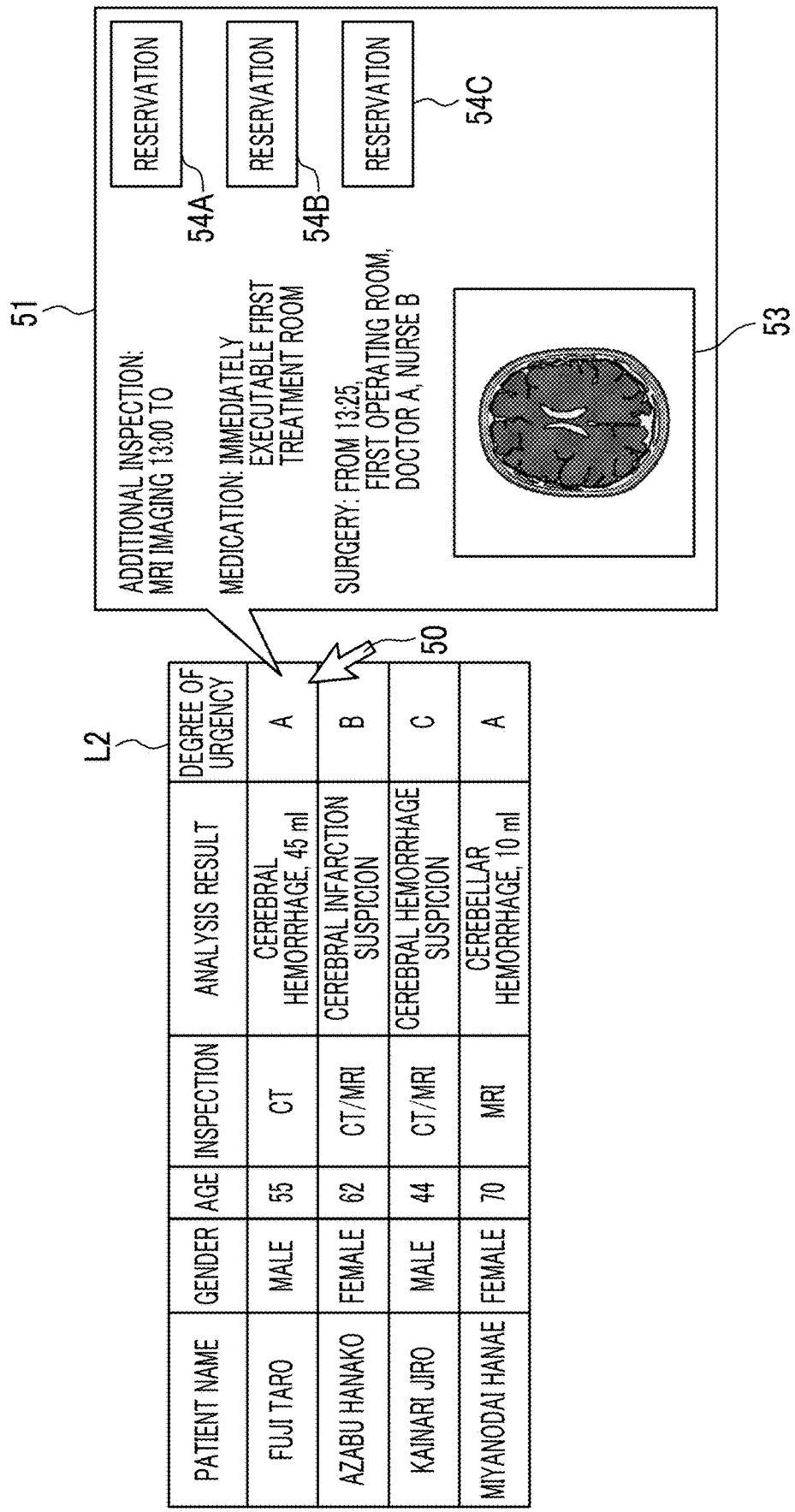

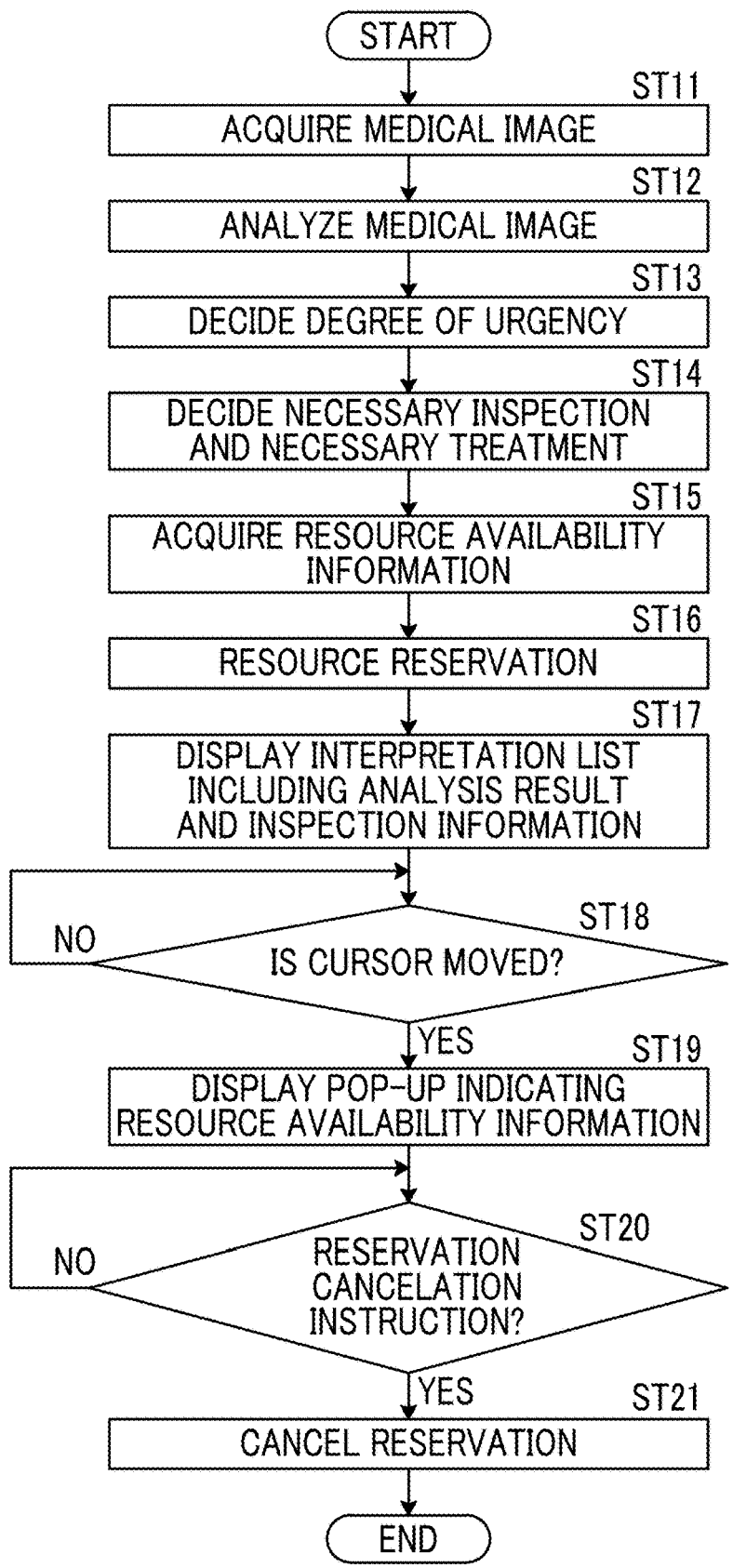

INSPECTION INFORMATION DISPLAY DEVICE, METHOD, AND PROGRAM

CROSS-REFERENCE TO RELATED APPLICATIONS

This application is a Continuation of PCT International Application No. PCT/JP2018/041962 filed on Nov. 13, 2018, which claims priority under 35 U. S. C. § 119(a) to Japanese Patent Application No. 2017-223629 filed on Nov. 21, 2017. Each of the above application(s) is hereby expressly incorporated by reference, in its entirety, into the present application.

BACKGROUND OF THE INVENTION

1. Field of the Invention

The present invention relates to inspection information display device, method, and program for displaying inspection information such as a patient name, a gender, and an age associated with data on a patient such as a medical image.

2. Description of the Related Art

In recent years, as medical devices such as a Computed Tomography (CT) device and Magnetic Resonance Imaging (MRI) have advanced, image diagnosis using medical images having higher quality and high resolution can be performed. In particular, in a case where a target portion is the brain, since a region having a vascular disorder such as cerebral infarction and cerebral hemorrhage can be specified by image diagnosis using CT images and MRI images, an appropriate treatment has been performed based on the specified result.

The medical image is analyzed by Computer-Aided Diagnosis (CAD) using a discriminator in which learning is performed by deep learning, and a bleeding region, an infarct region, and a bleeding volume in the brain, and an ischemic region in the heart are extracted. These regions are acquired as analysis results. As described above, an analysis result generated by analysis processing is stored in association with inspection information such as a patient name, a gender, an age, and a modality from which the medical image is acquired in a database, and is provided for diagnosis. At this time, a technician such as a radiologist who acquires the medical image decides a radiologist corresponding to the medical image, and informs the decided radiologist that there are the medical image and the analysis result using the CAD. The radiologist interprets the medical image and analysis result on his or her interpretation terminal while referring to the distributed medical image, and creates a radiology report.

In a case where the interpretation of the medical image is performed, an interpretation list of medical images to be interpreted is sent to an interpretation terminal. The interpretation list includes the aforementioned inspection information. As described above, a method of displaying a medical image to be desired to be interpreted first at the top of the interpretation list in a case where the interpretation list is displayed on the interpretation terminal has been suggested (see JP2007-094513A). A method of sorting the interpretation list according to a degree of severity of the patient and changing the allocation of the resource such as a nurse, an intern, a doctor, a technician, an intensive care specialist, or another healthcare professional based on the sorted result has been suggested (see JP2009-219867A).

SUMMARY OF THE INVENTION

Meanwhile, information necessary for creating the interpretation report such as a diagnosis name may not be able to be confirmed only from the medical image sent to the radiologist. The radiologist may determine that symptoms are so severe that an emergency operation is immediately required while looking at the medical image. In such a case, it is necessary for the radiologist to request treatments such as an inspection necessary to confirm the diagnosis name, capturing of a necessary medical image, and a care. In a case where the emergency operation is required, it is necessary to arrange an operating room, a surgeon, and a nurse. In order to perform such a request for the inspection and the treatment, it is necessary for the radiologist to confirm an availability situation of inspections, an availability situation of imaging rooms, an availability situation of operating rooms, schedules of surgeons, and schedules of nurses. Thus, a burden on the radiologist who arranges the inspection and the treatment is extremely large.

The present invention has been made in view of the aforementioned circumstances, and it is an object of the present invention to reduce a burden on an operator such as a radiologist at the time of arranging a necessary inspection and a necessary treatment by looking at inspection information.

An inspection information display device according to the present invention comprises a display controller that displays an inspection result obtained by analyzing data related to a patient and inspection information related to the data on a display unit, a decision unit that decides at least one of a necessary inspection or a necessary treatment for confirming the analysis result, and a resource information acquisition unit that acquires resource availability information for executing at least one of the necessary inspection or the necessary treatment. The display controller further displays the resource availability information on the display unit.

The "data" is data acquired as the result of the inspection and the capturing performed for the patient, and specifically, includes results of blood inspections, vital data such as an electrocardiogram and blood pressure, and image data such as medical images.

The "inspection information" means any information related to data such as a patient name, a gender, an age, and a modality from which the medical image is acquired.

The "necessary examination" includes the capturing of an additional medical image in addition to an additional inspection for confirming the analysis result.

The "necessary treatment" means any treatment performed for the patient such as care, medication, and surgery for the patient.

The "resource" means a facility and personnel required to perform a treatment method. Specifically, the resource includes any facility and personnel required for the treatment such as an inspection room, an imaging device for capturing other medical images, an operating room, surgeons, and nurses.

The inspection information display device according to the present invention may further comprise a resource reservation unit that performs a reservation of the resource according to a degree of urgency of the at least one of the necessary inspection or the necessary treatment.

The "reservation of the resource is performed according to the degree of urgency" means that the reservation of the resource is performed in a case where the degree of urgency is higher than a predetermined reference.

The inspection information display device according to the present invention may further comprise an input unit that receives an instruction of an operator. The resource reservation unit may cancel the reservation of the reserved resource by an input of the operator.

In the inspection information display device according to the present invention, in a case where the data is a medical image, the display controller may display the medical image on the display unit.

In this case, the display controller may display a minified picture of the medical image on the display unit.

An inspection information display method according to the present invention comprises displaying an analysis result obtained by analyzing data related to a patient and inspection information related to the data, deciding at least one of a necessary inspection or a necessary treatment for confirming the analysis result, acquiring resource availability information for executing the at least one of the necessary inspection or the necessary treatment, and displaying the resource availability information on the display unit.

A program causing a computer to execute the inspection information display method according to the present invention may be provided.

Another inspection information display device according to the present invention comprises a memory that stores a command to be executed by a computer, and a processor configured to execute the stored command. The processor executes processing of displaying an analysis result obtained by analyzing data related to a patient and inspection information related to the data, deciding at least one of a necessary inspection or a necessary treatment for confirming the analysis result, acquiring resource availability information for executing the at least one of the necessary inspection or the necessary treatment, and displaying the resource availability information on the display unit.

According to the present invention, the analysis result obtained by analyzing the data related to the patient and the inspection information related to the data are displayed, and at least one of the necessary inspection or the necessary treatment for confirming the analysis result is decided. The resource availability information for executing at least one of the necessary inspection or the necessary treatment is acquired, and the resource availability information is further displayed. Thus, the operator can easily know the resource availability information required to execute at least one of the necessary inspection or the necessary treatment. Therefore, it is possible to reduce a burden on the operator such as the reservation of the resources.

BRIEF DESCRIPTION OF THE DRAWINGS

FIG. 2 is a diagram showing a resource management database.

FIG. 8 is a diagram showing an urgency degree database.

FIG. 9 is a diagram showing an interpretation list including an analysis result and inspection information according to the second embodiment.

FIG. 10 is a flowchart showing processing performed in the second embodiment.

DESCRIPTION OF THE PREFERRED EMBODIMENTS

Figure 1:
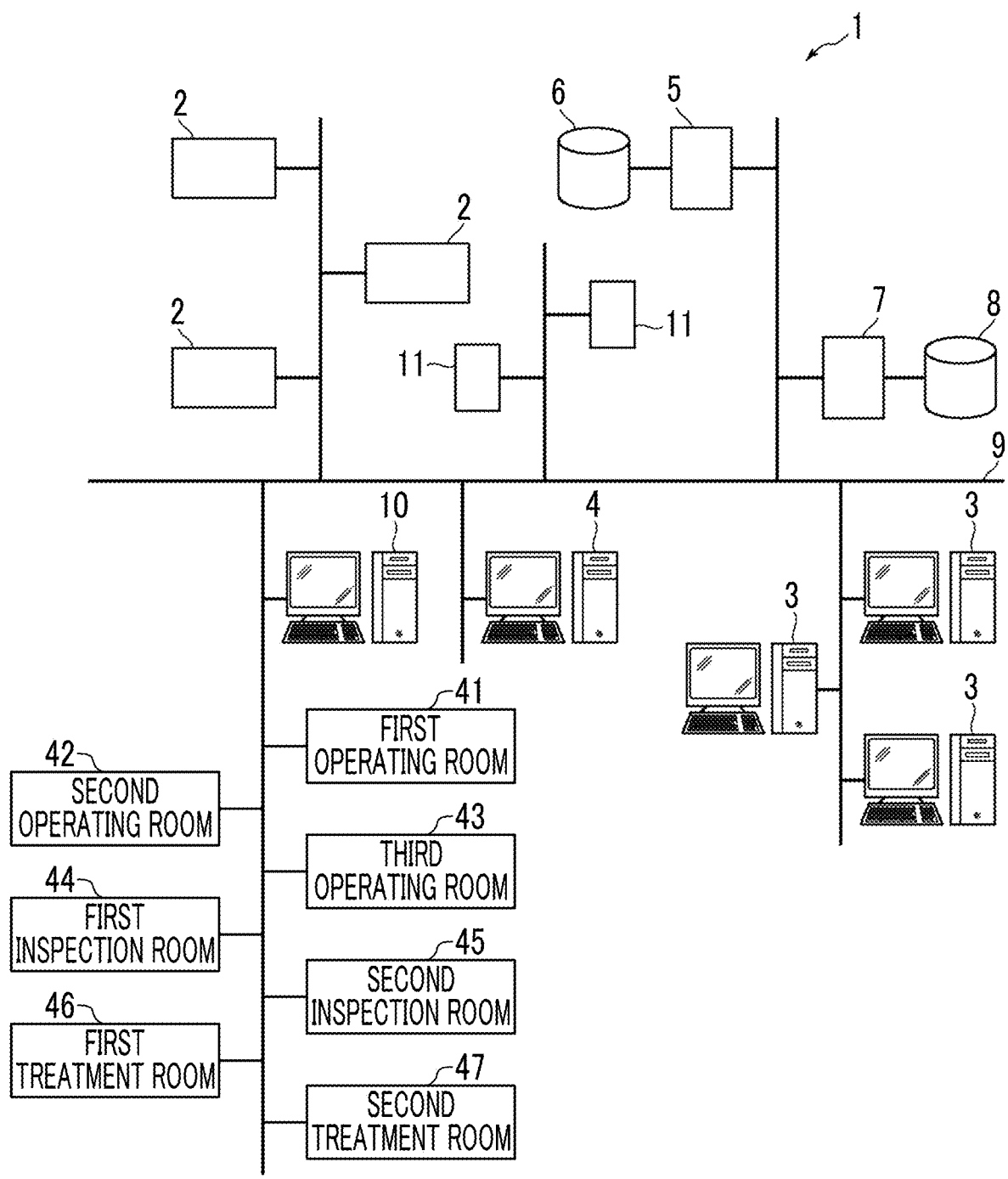
FIG. 1 is a diagram showing a schematic configuration of a medical information system to which an inspection information display device according to an embodiment of the present invention is applied.

Hereinafter, embodiments of the present invention will be described with reference to the drawings. FIG. 1 is a diagram showing a schematic configuration of a medical information system to which an inspection information display device according to an embodiment of the present invention is applied. The medical information system 1 shown in FIG. 1 is a system configured to capture an inspection target portion of a subject based on an inspection order from a doctor in a clinical department using a known ordering system, store a medical image acquired by the capturing, perform medial interpretation by a radiologist and creation of an interpretation report, and perform browsing of the interpretation report by the doctor in the clinical department as a requesting party and detailed observation of the medical image to be interpreted. As shown in FIG. 1, the medical information system 1 is configured such that a plurality of modalities (imaging devices) 2, a plurality of interpretation workstations (WS) 3 which is interpretation terminals, a clinical department workstation (WS) 4, an image server 5, an image database 6, an interpretation report server 7, an interpretation report database 8, a resource management system 10, and a portable terminal 11 of a hospital staff (doctor or nurse) are connected to be able to communicate with each other via a wired or wireless network 9. The inspection information display device according to the present embodiment is applied to the interpretation WS 3.

Each device is a computer on which an application program for functioning as a component of the medical information system 1 is installed. The application program is distributed while being recorded on a recording medium such as a Digital Versatile Disc (DVD) or a Compact Disc Read Only Memory (CD-ROM), and is installed on the computer from the recording medium. Alternatively, the application program is stored in a storage device of a server computer connected to a network or a network storage in a state of being accessible from the outside, and is downloaded and installed on the computer according to a request.

The modality 2 is a device that generates a medical image representing a diagnosis target portion by capturing the diagnosis target portion of the subject. Specifically, the modality is a CT device, an MRI device, and a Positron Emission Tomography (PET) device. The medical image generated by the modality 2 is transmitted to the image server 5 and stored.

The interpretation WS 3 includes the inspection information display device according to the first embodiment. A configuration of the interpretation WS 3 will be described below.

The clinical department WS 4 is a computer that is used by the doctor in the clinical department for the detailed observation of the image, browsing of the interpretation report, and creation of an electronic medical record, and includes a processing device, a high-definition display, and input devices such as a keyboard and a mouse. In the clinical department WS 4, each processing of a browsing request for an image to the image server 5, display of an image received from the image management server 5, automatic detection or emphasis display of a lesion-like portion in the image, and a browsing request of an interpretation report to the interpretation report server 7, and display of the interpretation report received from the interpretation report server 7 is performed by executing a software program for each processing.

The image server 5 is a general-purpose computer on which a software program for providing a function of a database management system (DBMS) having a relatively high processing capability is installed. The image server 5 has a large-capacity storage including the image database 6. This storage may be a large-capacity hard disk device connected to the image server 5 by a data bus, or may be a disk device connected to a Network Attached Storage (NAS) and a Storage Area Network (SAN) connected to the network 9. In a case where a registration request for the medical image from the modality 2 is received, the image server 5 prepares the medical image in a database format, and registers the medical image in the image database 6.

In the image database 6, image data of the medical image acquired in the modality 2 and accessory information are registered. The accessory information may include, for example, an image ID for identifying an individual medical image, a patient identification (ID) for identifying a subject, an inspection ID for identifying an inspection, a unique identification (UID) assigned to each medical image, an inspection date and an inspection time at which the medical image is generated, a type of the modality used in the inspection for acquiring the medical image, patient information such as a patient name, an age, and a gender, an inspection portion (imaging portion), imaging information (imaging protocol, imaging sequence, imaging method, imaging condition, and use of contrast agent), and information of a series number or a collection number in a case where a plurality of medical images is acquired in one inspection.

In a case where the browsing request from the interpretation WS 3 is received via the network 9, the image server 5 searches for the medical image registered in the image database 6, and transmits the extracted medical image to the interpretation WS 3 as the requesting party.

The interpretation report server 7 incorporates a software program that provides a function of a database management system to a general-purpose computer. In a case where a registration request for the interpretation report from the interpretation WS 3 is received, the interpretation report server 7 prepares the interpretation report in a database format, and registers the interpretation report in the interpretation report database 8.

For example, an interpretation report in which information such as an image ID for identifying the medical image to be interpreted, a radiologist ID for identifying an image radiologist who performs interpretation, a lesion name, positional information of a lesion, a medical opinion, and a degree of certainty of the medical opinion is recorded is recorded in the interpretation report database 8.

The network 9 is a wired or wireless local area network for connecting various devices in a hospital. In a case where the interpretation WS 3 is installed in another hospital or clinic, the network 9 may have a configuration in which local area networks of the hospitals are connected to each other via the Internet or a dedicated line. In any case, it is preferable that the network 9 has a configuration capable of realizing high-speed transfer of the medical images such as an optical network.

The resource management system 10 is a computer that manages facilities and personnel necessary for executing various treatment methods in the hospital, and includes a processing device, a display, and input devices such as a keyboard and a mouse. The resource management system 10 manages schedules of resources for performing inspections and treatments in the hospital such as schedules for first to third operating rooms 41 to 43, schedules for first and second inspection rooms 44 and 45, schedules for first and second treatment rooms 46 and 47, schedules of the plurality of modalities 2, doctors in the hospital, particularly, schedules of surgeons of surgeries, and schedules of nurses shown in FIG. 1.

The management of the schedules of the first to third operating rooms 41 to 43 is performed based on inputs from terminals installed in the first to third operating rooms 41 to 43 and an input from a terminal of a doctor in charge of a patient to be operated. The inspection room is an inspection room for performing various inspections such as an electrocardiogram measurement and a blood inspection. Although it has been described in the present embodiment that two inspection rooms are provided, three or more inspection rooms may be provided. The management of the schedules of the first and second inspection rooms 44 and 45 is performed based on the inputs from the terminals set in the first and second inspection rooms 44 and 45 or the input from the terminal of the doctor in charge of the patient to be operated. The treatment room is a room for performing treatment and preparation using medication. Although it has been described in the present embodiment that two treatment rooms are provided, three or more treatment rooms may be provided. The management of the schedules of the first and second treatment rooms 46 and 47 is performed based on the inputs from the terminals set in the first and second treatment rooms 46 and 47 and the input from the terminal of the doctor in charge of the patient to be operated. The management of the schedules of the doctors and the nurses in the hospital is performed based on inputs from terminals of the doctors and the nurses. The management of the schedules of the modalities 2 is performed based on inputs from terminals of imaging rooms where the modalities 2 are installed and an input from a terminal of a doctor in charge of a patient to be imaged.

In the present embodiment, the first and second inspection rooms 44 and 45 and the modalities 2 are resources for executing the inspection. The first to third operating rooms 41 to 43, the first and second treatment rooms 46 and 47, and the doctors and the nurses are resources for executing the treatment.

Figures 3, 4:
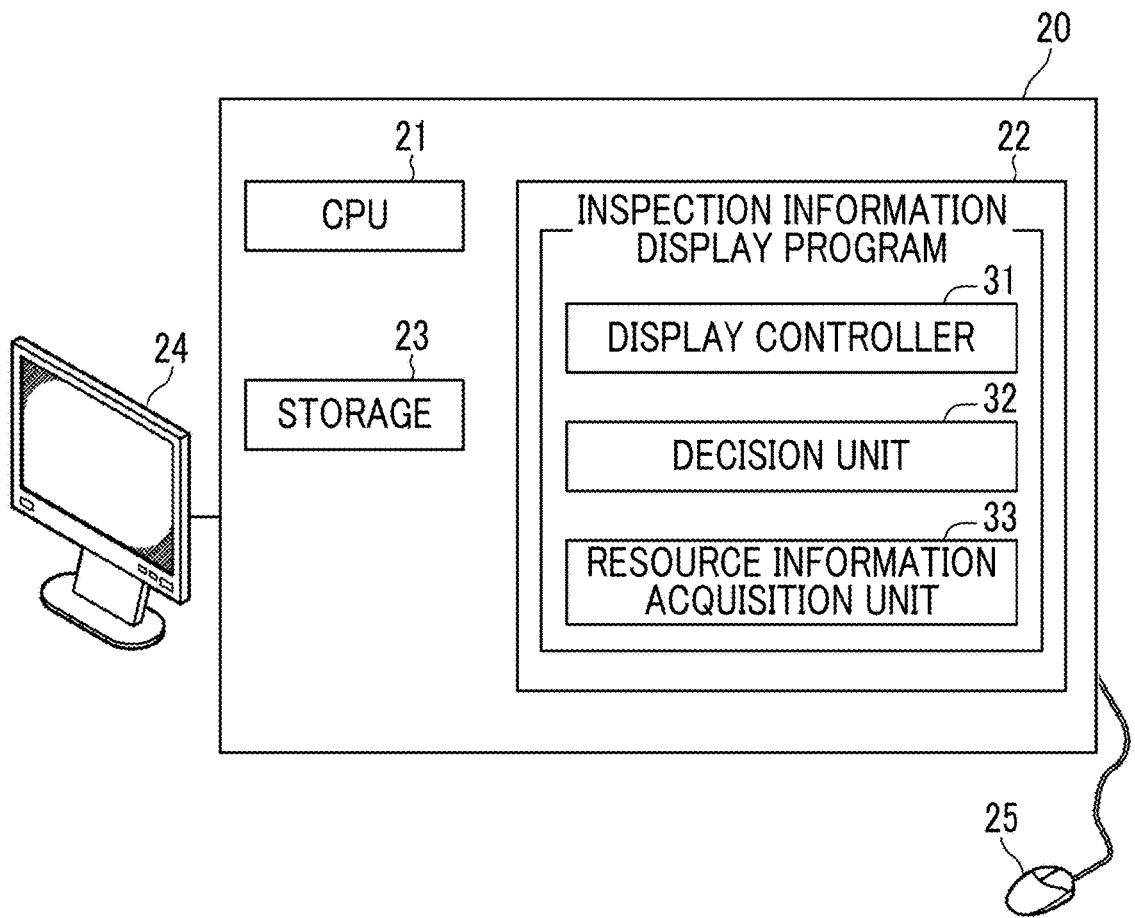
FIG. 3 is a diagram showing a schematic configuration of an inspection information display device according to a first embodiment of the present invention.
FIG. 4 is a diagram showing an inspection treatment database.

The resource management system 10 manages resources using a resource management database. FIG. 2 is a diagram showing the resource management database. As shown in FIG. 3, a resource management database DB1 manages various resources, that is, the schedules of the first to third operating rooms 41 to 43, the first and second inspection rooms 44 and 45, the first and second treatment rooms 46 and 47, doctors A and B, nurses A and B, and a CT device and an MRI device as the modalities 2. That is, the date and time, and a time at which the resource is used at this date and time (in the case of the doctors and the nurses, a scheduled time) are indicated for various resources. FIG. 2 shows the schedules of the resources on November 21. In FIG. 2, the time for which the resource is used is indicated by a double-headed arrow.

Hereinafter, the interpretation WS 3 according to the present embodiment will be described in detail. The interpretation WS 3 is a computer to be used by the radiologist of the medical image for the interpretation of the medical image and the creation of the interpretation report, and includes a processing device, a high-definition display, and input devices such as a keyboard and a mouse. In the interpretation WS 3, various processing such as the browsing request for the medical image to the image server 5, various image processing on the medical image received from the image server 5, the display of the medical image, the automatic detection and the emphasis display of a structure and a lesion-like portion in the medical image by analyzing the medical image, support of the creation of the interpretation report, the registration request and the browsing request for the interpretation report to the interpretation report server 7, and interpretation report creation request, the registration request and the browsing request of the interpretation report to the interpretation report server, and the display of the interpretation report received from the interpretation report server 7 is performed by executing the software program for performing each processing. Since these processing is performed by a well-known software program, detailed description thereof is omitted herein. A separate image processing server and an analysis server may be connected to the network 9 without performing various image processing and the analysis of the medical image in the interpretation WS 3, and the image processing server and the analysis server may perform the various image processing and the analysis of the medical image according to the processing request from the interpretation WS 3.

The interpretation WS 3 includes the inspection information display device according to the first embodiment. Thus, the inspection information display program according to the first embodiment is installed on the interpretation WS 3. The inspection information display program is distributed while being recorded on a recording medium such as a DVD or a CD-ROM, and is installed on the interpretation WS 3 from the recording medium. Alternatively, the interpretation information display program is stored in the storage device of the server computer connected to the network or the network storage in a state of being accessible from the outside, and is downloaded and installed in the interpretation WS 3 according to a request.

FIG. 3 is a diagram showing a schematic configuration of the inspection information display device according to the first embodiment of the present invention which is realized by installing the inspection information display program. As shown in FIG. 3, an inspection information display device 20 includes, as a standard computer configuration, a Central Processing Unit (CPU) 21, a memory 22, and a storage 23. A display 24 such as a high-definition liquid crystal display and an input unit 25 such as a keyboard and a mouse are connected to the inspection information display device 20.

The storage 23 includes a storage device such as a hard disk or a Solid State Drive (SSD). The storage 23 stores various information including the medical images and information necessary for processing of the inspection information display device 20, which is acquired from the image server 5 via the network 9.

The memory 22 stores the inspection information display program. The inspection information display program prescribes, as processing to be executed by the CPU 21, display control processing for displaying an analysis result obtained by analyzing data related to a patient, inspection information related to the data, and resource availability information to be described below on the display 24, decision processing for deciding at least one of necessary inspection or necessary treatment for confirming the analysis result, and resource information acquisition processing for acquiring the resource availability information for executing at least one of the necessary inspection or the necessary treatment. The inspection information display device 20 receives a notification that a new medical image to be interpreted is stored in the image server 5, and thus, these processing is performed.

The CPU 21 executes these processing according to the program, and thus, the computer functions as a display controller 31, a decision unit 32, and a resource information acquisition unit 33. Although it has been described in the present embodiment that the CPU 21 executes the functions of the units by the inspection information display program, a programmable logic device (PLD) which is a processor of which a circuit configuration is changeable after a Field Programmable Gate Array (FPGA) is manufactured can be used as a general-purpose processor that functions as various processing units by executing software in addition to the CPU 21. The processing of each unit may be executed by a dedicated electric circuit which is a processor having a circuit configuration specifically designed to execute specific processing such as an Application Specific Integrated Circuit (ASIC).

One processing unit may be constituted by one of these various processors, or may be a combination of two or more processors of the same type or different types (for example, a combination of a plurality of FPGAs or a combination of a CPU and an FPGA). A plurality of processing units may be constituted by one processor. As an example in which the plurality of processing units is constituted by one processor, first, one processor is constituted by a combination of one or more CPUs and software and this processor functions as the plurality of processing units as represented by a computer such as a client or a server. Second, a processor that realizes the functions of the entire system including the plurality of processing units by using one Integrated Circuit (IC) chip is used as represented by a System On Chip (SoC). As described above, the various processing units are constituted by using one or more of the aforementioned various processors as a hardware structure.

The hardware structure of these various processors is more specifically an electric circuitry in which circuit elements such as semiconductor elements are combined.

In a case where the interpretation WS 3 functions as a device that performs processing other than the inspection information display device 20, a program for executing this function is stored in the memory 22. For example, in a case where the analysis processing of the medical image is performed, an analysis program is stored.

The display controller 31 displays the analysis result obtained by analyzing the data related to the patient, the inspection information related to the data, and the resource availability information. Here, in the present embodiment, it is assumed that the data is the medical image acquired by capturing the patient by using the modality 2. The analysis result is acquired by the analysis program installed on the interpretation WS 3. For example, in a case where the medical image is a CT image of the brain, the analysis result includes a bleeding region, an infarct region, and a bleeding volume specified in the brain. The inspection information includes information such as a patient name, a gender, an age, and the modality from which the medical image is acquired. The inspection information is acquired from the image database 6. The display controller 21 displays the analysis result and the inspection information, as an interpretation list which is a list of the medical images to be interpreted. Since the interpretation list includes the resource availability information to be described below, the display of the interpretation list will be described below.

The decision unit 32 decides at least one of the necessary inspection or the necessary treatment for confirming the analysis result. Although it has been described in the present embodiment that both the necessary inspection and the necessary treatment are decided, only the necessary inspection or only the necessary treatment may be decided. Thus, the inspection information display device 20 according to the present embodiment stores a database in which the analysis result is associated with the inspection and the treatment in the storage 23. Hereinafter, this database is referred to as an inspection treatment database. FIG. 4 is a diagram showing the inspection treatment database. As shown in FIG. 4, a portion, a symptom for the portion, and a treatment method for the symptom are associated with each other in an inspection treatment database DB2. For example, in a case where the portion is the brain, the symptom is associated with bleeding and infarction, and the bleeding is associated with CT imaging, MRI imaging, medication, and surgery as the inspection and the treatment.

The decision unit 32 decides, as the inspection and the treatment necessary to confirm the analysis result, an inspection and a treatment other than the inspection and the treatment being already performed while referring the inspection treatment database DB2. For example, in a case where the imaging portion is the brain and the analysis result is bleeding and the inspection information is based on the medical image acquired by CT imaging, MRI imaging, medication, and surgery are decided as the necessary inspection and the necessary treatment for confirming the analysis result.

The resource information acquisition unit 33 acquires the resource availability information in order to execute the necessary inspection and the necessary treatment in order to decide the analysis result which is decided by the decision unit 32. Specifically, the resource information acquisition unit checks the schedules of the resources for executing the decided inspection and treatment, and acquires the resource availability information while referring to the resource management database DB1 managed by the resource management system 10. For example, in a case where the decided inspection includes MRI imaging, a date and time at which the MRI imaging is executable is acquired as the availability information while referring to the schedule of the MRI device of the modality 2. In a case where the decided treatment includes medication, the schedules of the first and second treatment rooms 46 and 47 are checked, and a date and time at which medication is executable is acquired as the availability information. In a case where the decided treatment includes surgery, the schedules of the first to third operating rooms 41 to 43, a date and time at which the surgery is executable is acquired as the availability information while referring to the schedules of the surgeon and the nurse.

Figure 5:
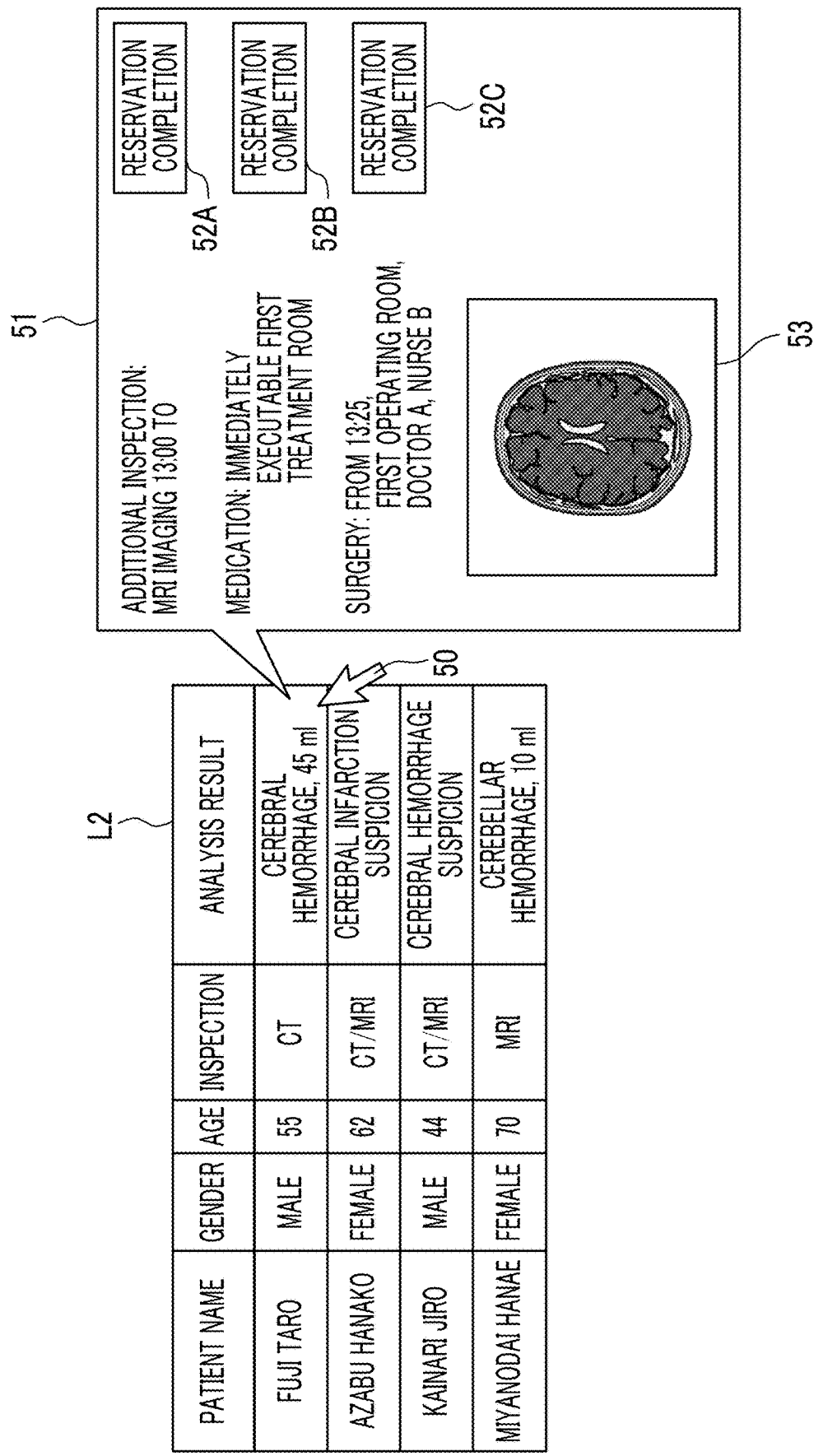
FIG. 5 is a diagram showing an interpretation list including an analysis result and inspection information according to the first embodiment.

The display controller 31 displays the interpretation list including the analysis result and the inspection information, as described above. FIG. 5 is a diagram showing the interpretation list including the analysis result and the inspection information. As shown in FIG. 5, an interpretation list L1 shows a patient name, a gender, an age, inspection information indicating a performed inspection, and an analysis result. The radiologist moves a cursor 50 to a column of a desired patient name on the interpretation list L1 by operating the input unit 25. Accordingly, a pop-up 51 indicating the resource availability information is displayed. As shown in FIG. 5, the pop-up 51 indicates that additional inspection, medication, and surgery are decided as the necessary inspection and the necessary treatment for confirming the analysis result, that the additional inspection is MRI imaging and is executable from 13:00, that medication is immediately executable in the first treatment room, and that surgery is executable by a doctor A and a nurse B and is executable in the first operating room from 13:25.

The pop-up 51 includes reservation buttons 52A, 52B, and 52C for executing a reservation for each inspection and treatment. The pop-up 51 includes a minified picture 53 of the medical image. The radiologist can reserve the necessary inspection and treatment from the interpretation WS 3 by clicking the reservation button for the necessary inspection and treatment. The reservation of the necessary inspection and treatment is to transmit information indicating that the reservation for the resource for executing the inspection and the treatment is made. At this time, the radiologist can perform a certain degree of interpretation without displaying the medical image while referring to the minified picture 53 included in the pop-up 51. Therefore, the minified picture 53 can assist the radiologist in executing the reservation for the inspection and the treatment. Here, the information indicating that the reservation for the surgeon and the nurse is made is transmitted to the portable terminals 11 owned by the surgeon and the nurse.

The display controller 31 may display the interpretation list L1 on the display 24 before the resource availability information is acquired. In this case, after the resource availability information is acquired, the pop-up 51 indicating the necessary inspection and treatment is displayed due to the movement of the cursor 50.

Figure 6:
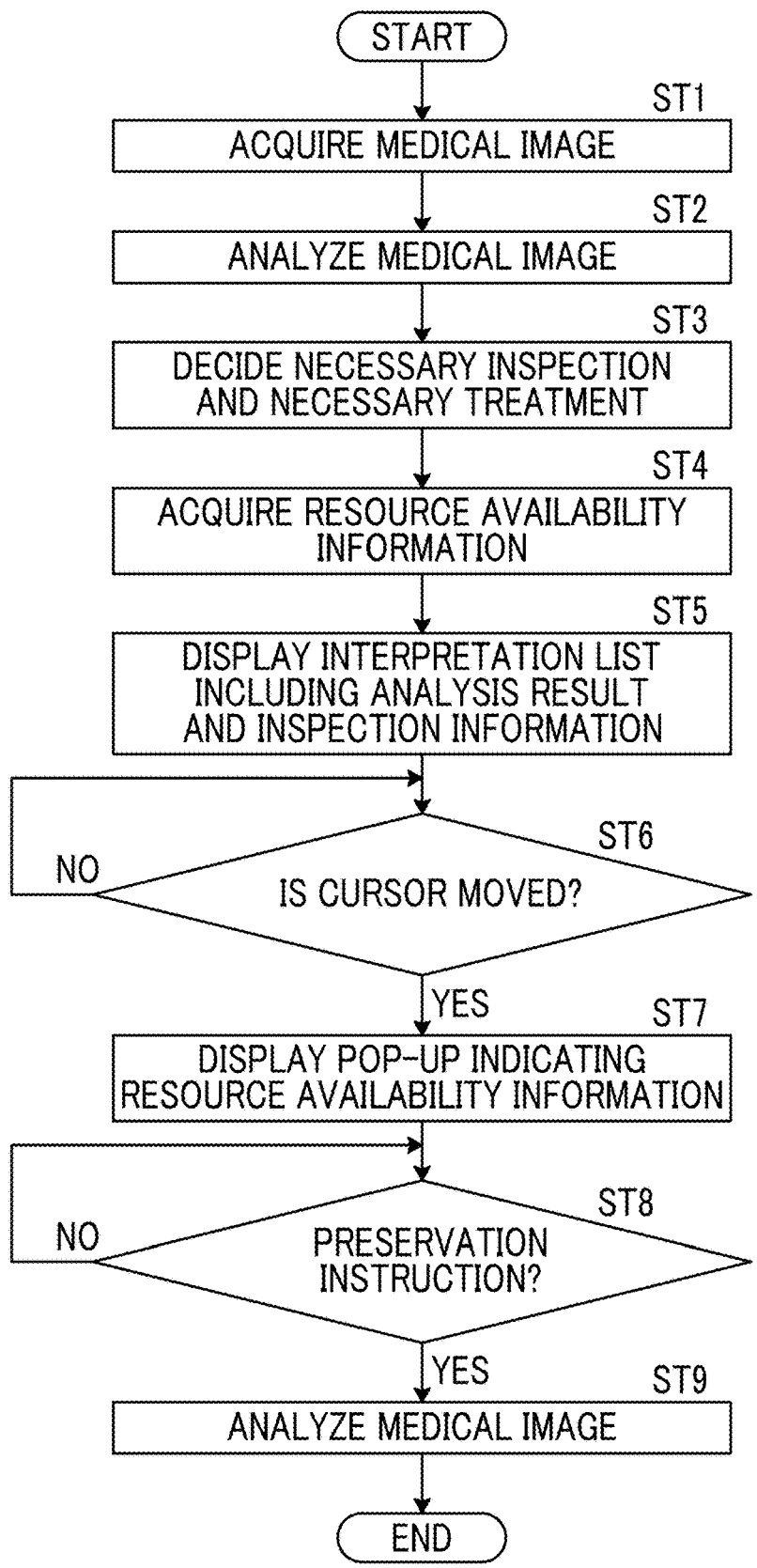
FIG. 6 is a flowchart showing processing performed in the first embodiment.

Next, processing performed in the first embodiment will be described. FIG. 6 is a flowchart showing the processing performed in the first embodiment. The interpretation WS 3, that is, the inspection information display device 20 receives a notification indicating that a new medical image is stored in the image server 5, and thus, processing is started. Subsequently, the medical image is acquired from the image server 5 by the analysis program installed on the interpretation WS 3 (step ST1). Thereafter, the medical image is analyzed, and the analysis result is acquired (step ST2).

Subsequently, the decision unit 32 decides the necessary inspection and the necessary treatment for confirming the analysis result (step ST3), and the resource information acquisition unit 33 acquires the resource availability information for executing the inspection and the treatment decided by the decision unit 32 (step ST4). The display controller 31 displays the interpretation list L1 including the analysis result and the inspection information on the display 24 (step ST5). In this state, monitoring of whether or not the cursor 50 is moved to the column of the specific patient on the interpretation list L1 is started (step ST6). In a case where the result of step ST6 is positive, the display controller 31 displays the pop-up 51 indicating the resource availability information for executing the necessary inspection and the necessary treatment for confirming the analysis result for the patient to which the cursor 50 is moved (step ST7). In a case where the pop-up 51 is displayed, monitoring of whether or not a reservation instruction is issued for the inspection and the treatment decided by the decision unit 32 is started by using the reservation buttons 52A to 52C included in the pop-up 51 (step ST8). In a case where step ST8 is positive, the reservation for the instructed inspection and treatment is executed for the resource (step ST9), and the processing ends.

As described above, according to the present embodiment, it has been described that at least one of the necessary inspection or the necessary treatment for confirming the analysis result is decided, the resource availability information for executing the required inspection and the necessary treatment is acquired, and the resource availability information is displayed. Thus, an operator can easily know the resource availability information required for executing the necessary inspection and the necessary treatment for confirming the analysis result. Therefore, it is possible to reduce a burden on the operator such as the reservation of the resources.

Figure 7:
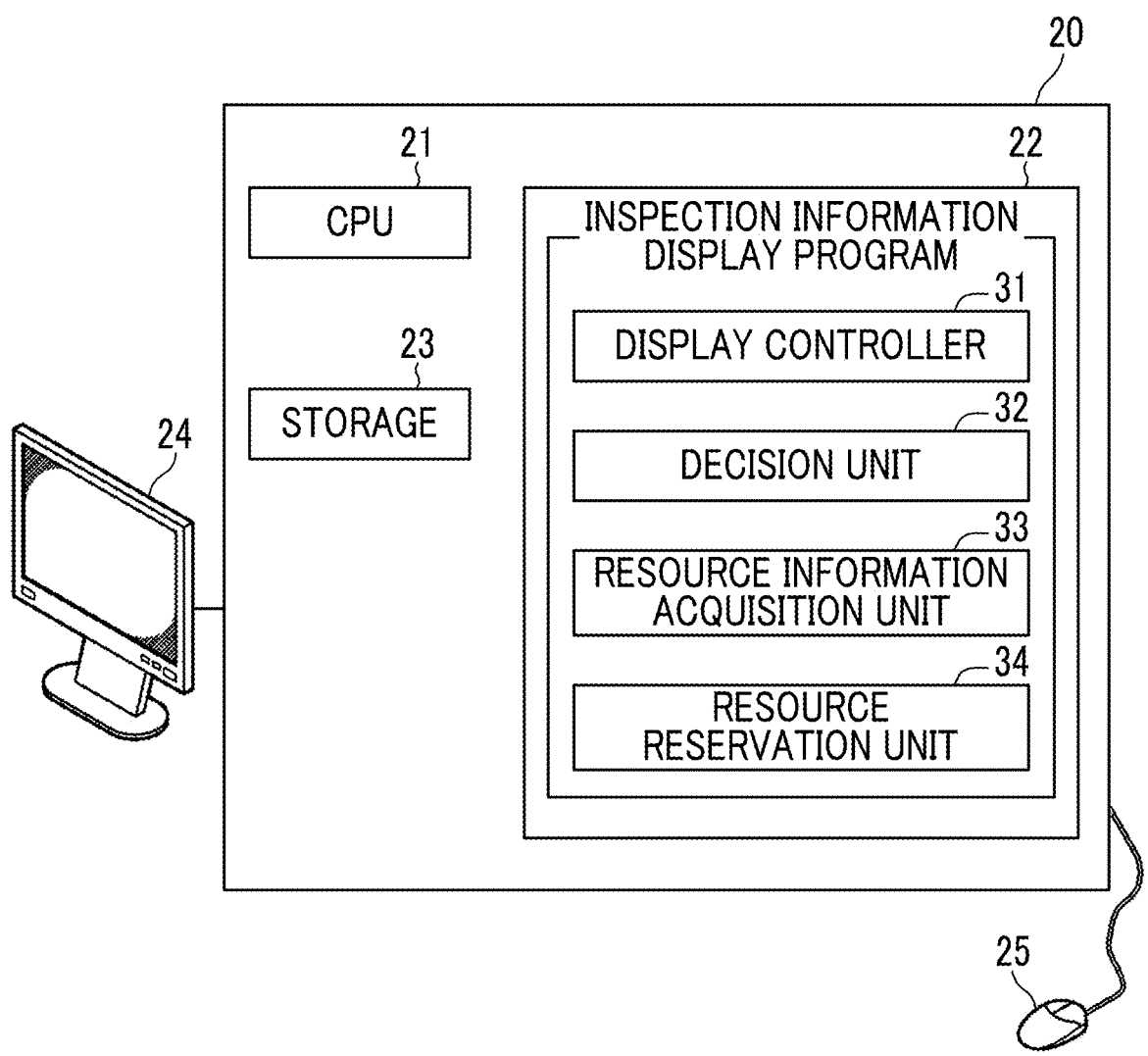
FIG. 7 is a diagram showing a schematic configuration of an inspection information display device according to a second embodiment of the present invention.

Next, a second embodiment of the present invention will be described. FIG. 7 is a diagram showing a schematic configuration of the inspection information display device according to the second embodiment of the present invention. In FIG. 7, the same components as those in FIG. 3 are denoted by the same references, and detailed description is omitted. As shown in FIG. 7, the inspection information display device 20 according to the second embodiment is different from the first embodiment in that a resource reservation unit 34 that performs the reservation of the resource according to a degree of urgency of the necessary inspection and the necessary treatment for confirming the analysis result. The resource reservation unit 34 also cancels the reservation of the resource according to the input from the input unit 25.

The degree of urgency is acquired by the analysis program installed on the interpretation WS 3. Specifically, the degree of urgency of the interpretation for the medical image is acquired based on the analysis result of the medical image. Thus, the analysis program decides the degree of urgency while referring to an urgency degree database in which various analysis results are associated with degrees of urgency. The urgency degree database is stored in the storage 23.

FIG. 8 is a diagram showing the urgency degree database. As shown in FIG. 8, the urgency degree database DB3 associates bleeding portions (for example, putaminal hemorrhage, subcortical hemorrhage, and cerebellar hemorrhage in the brain) related to the bleeding region with the degree of urgency corresponding to the bleeding volume. As the amount of bleeding becomes larger, the degree of urgency becomes higher in the order of C, B, and A. For example, in a case where the bleeding portion is subcortical bleeding and the bleeding volume is 50 ml, the degree of urgency is decided to be A by referring to the urgency degree database DB3.

The degree of urgency may be decided by a discriminator in which learning is performed so as to input the analysis result and output an evaluation value for deciding the degree of urgency. The evaluation value expresses, for example, the degree of urgency as a value between 0 and 1. It is assumed that as the value becomes larger, the degree of urgency becomes higher. In this case, the degree of urgency is decided according to the evaluation value. For example, the degree of urgency is decided such that the evaluation value is 0 or more and is less than 0.33, the degree of urgency C is 0.33 or more and is less than 0.66, and the degree of urgency B is 0.66 or more and is 1.0 or less.

In a case where the degree of urgency is decided to be A, the resource reservation unit 34 executes the reservation for the resource for executing the necessary inspection and the necessary treatment in order to specify the analysis result which is decided by the decision unit 32. That is, the resource reservation unit executes the reservation of the resource while referring to the resource availability information acquired by the resource information acquisition unit 33. In a case where the degree of urgency is decided to be B or C, the resource reservation unit 34 does not execute the reservation of the resource for executing the necessary inspection and the necessary treatment in order to specify the analysis result.

In the second embodiment, the display controller 31 displays the degree of urgency on the interpretation list including the analysis result and the inspection information. FIG. 9 is a diagram showing the interpretation list including the analysis result and the inspection information to be displayed in the second embodiment. As shown in FIG. 9, an interpretation list L2 shows the degree of urgency in addition to the patient name, the gender, the age, the inspection information indicating the performed inspection, and the analysis result. The radiologist moves the cursor 50 to the column of the patient name on the interpretation list L2 by operating the input unit 25. Accordingly, the pop-up 51 indicating the resource availability information is displayed. As shown in FIG. 9, the pop-up 51 in the second embodiment indicates that additional inspection, medication, and surgery are decided as the necessary inspection and the necessary treatment for confirming the analysis result, that the additional inspection is MRI imaging and is executable from 13:00, that medication is immediately executable in the first treatment room, and that surgery is executable by the doctor A and the nurse B and is executable in the first operating room from 13:25. In the second embodiment, the pop-up 51 includes reservation completion buttons 54A, 54B, and 54C indicating that the reservation of the resources is completed for the inspection and the treatment. The pop-up 51 includes a minified picture 53 of the medical image.

In the second embodiment, in a case where the radiologist considers that it is not necessary to execute the reservation of the resources for the necessary inspection and the necessary treatment for confirming the analysis result, the reservation of the reserved resource can be released by clicking the reservation completion button for the unnecessary inspection and treatments. The cancelation of the reservation of the unnecessary inspection and treatment is to transmit information indicating that the reservation is canceled for the reserved resource.

Next, processing performed in the second embodiment will be described. FIG. 10 is a flowchart showing the processing performed in the second embodiment. The interpretation WS 3, that is, the inspection information display device 20 receives the notification indicating that the new medical image is stored in the image server 5, and thus, processing is started. Subsequently, the medical image is acquired from the image server 5 by the analysis program installed on the interpretation WS 3 (step ST11). Thereafter, the medical image is analyzed, and the analysis result is acquired (step ST12). The degree of urgency is decided based on the analysis result (step ST13).

Subsequently, the decision unit 32 decides the necessary inspection and the necessary treatment in order to decide the analysis result (step ST14), and the resource information acquisition unit 33 acquires the resource availability information for executing the inspection and the treatment decided by the decision unit 32 (step ST15). The resource reservation unit 34 performs the reservation of the resource according to the degree of urgency of the inspection and the treatment (step ST16). The display controller 31 displays the interpretation list L2 including the analysis result and the inspection information on the display 24 (step ST17). In this state, monitoring of whether or not the cursor 50 is moved to the column of the specific patient on the interpretation list L2 is started (step ST18). In a case where the result of step ST18 is positive, the display controller 31 displays the pop-up 51 indicating the resource availability information for executing the necessary inspection and the necessary treatment for confirming the analysis result for the patient to which the cursor 50 is moved (step ST19). In a case where the pop-up 51 is displayed, monitoring of whether or not a reservation cancelation instruction is issued for the inspection and the treatment decided by the decision unit 32 is started by using the reservation completion buttons 54A to 54C included in the pop-up 51 (step ST20). In a case where step ST20 is positive, the reservation cancelation instruction for the designated inspection and treatment is issued for the resource (step ST21), and the processing ends.

As described above, in the second embodiment, since the reservation of the resource is performed according to the degree of urgency of the necessary inspection and the necessary treatment for confirming the analysis result, the burden on the operator in a case where the reservation is performed can be reduced.

Since the reserved resource is canceled by the input of the operator, it is possible to prevent the unnecessary resource from being reserved forever, and thus, it is possible to allocate the resource to the person who needs the resource.

Although it has been described in the aforementioned second embodiment that the reservation is canceled by an instruction for the reservation completion buttons 54A to 54C, the degree of urgency may be changed as a result by interpreting the medical image by the radiologist. For example, in a case where the degree of urgency is A, the degree of urgency may be changed to B or C. As described above, in a case where the degree of urgency is changed from A to B or C by the radiologist, the resource reservation unit 34 may cancel the reserved reservation. In contrast, in a case where the degree of urgency of B or C is changed to A by the radiologist, the resource reservation unit 34 may perform the reservation of the resource for executing the treatment method.

Although it has been described in each of the aforementioned embodiments that the pop-up 51 indicating the resource availability information is displayed by issuing the instruction using the cursor 50 in the interpretation lists L1 and L2, the resource availability information may be displayed on the interpretation lists L1 and L2.

Although it has been described in each of the aforementioned embodiments that the decision unit 32 decides the necessary inspection and the necessary treatment for confirming the analysis result while referring to the inspection treatment database DB1, the necessary inspection and the necessary treatment for confirming the analysis result may be decided by the input of the operator from the input unit 25.

The burden on the operator in a case where the reservation of the resource is performed can be reduced by performing the reservation of the resource according to the degree of urgency of at least one of the necessary inspection or the necessary treatment.

The reserved resource is canceled according to the input of the operator, and thus, it is possible to prevent the unnecessary resource from being reserved forever. Accordingly, it is possible to allocate the resource to the person who needs the resource.

In a case where the data is the medical image, the medical image is displayed on the display unit, and thus, the operator can see the medical image. Accordingly, it is possible to determine the validity of the analysis result.

EXPLANATION OF REFERENCES

1: medical information system
2: modality
3: interpretation workstation
4: clinical department workstation
5: image server
6: image database
7: interpretation report server
8: interpretation report database
9: network
10: resource management system
11: portable terminal
21: CPU
22: memory
23: storage
24: display
25: input unit
31: display controller
32: decision unit
33: resource information acquisition unit
34: resource reservation unit
41 to 43: operating room
44, 45: inspection room
46, 47: treatment room
50: cursor
51: pop-up display
52A to 52C: reservation button
53: minified picture
54A to 54C: reservation cancelation button
DB1: resource management database
DB2: inspection treatment database
DB3: urgency degree database
L1, L2: interpretation list

What is claimed is:
1. An inspection information display device comprising:
a storage medium storing at least an inspection treatment database; and
a processor coupled to the display unit and the storage medium and controlled at least to:
control the display unit to display an analysis result obtained by analyzing data related to a patient and inspection information related to the data on a display unit;
determine at least one of a necessary inspection or a necessary treatment to confirm the analysis result by referring to the inspection treatment database which includes multiple entries with each of the multiple entries associates among a human portion, a symptom, and a necessary inspection or a necessary treatment and by selecting the necessary inspection or the necessary treatment according to a corresponding human portion and symptom;
acquire the resource availability information to determine at least a location for executing the at least one of the selected necessary inspection or the necessary treatment;
detect, as shown on the display unit, a cursor being on the analysis result or on a degree of urgency field;
display in a pop-up menu that indicating resource availability information, the selected at least one of the necessary inspection or the necessary treatment, and the determined location for performing the selected at least one of the necessary inspection or the necessary treatment in response to detecting the cursor being on the analysis result, wherein the pop-up menu as the result of detecting the cursor being on the analysis result further comprises:
  a first region upon which an activation of the first region reserves, at a first determined location from the resource availability information, a first necessary inspection or a first necessary treatment specified in the inspection treatment database, and
  a second region upon which an activation of the second region reserves, at a second determined location from the resource availability information, a second necessary inspection or a second necessary treatment specified in the inspection treatment database;
perform in the pop-up menu a reservation for the at least one of the necessary inspection or the necessary treatment based on the resource availability information by activating the first region or the second region
display in a pop-up menu that indicating resource availability information, the selected at least one of the necessary inspection or the necessary treatment, and the determined location for performing the selected at least one of the necessary inspection or the necessary treatment in response to detecting the cursor being on the degree of urgency field; wherein the pop-up menu as the result of detecting the cursor being on the degree of urgency field further comprises
  a third region upon which an activation of the third region cancels, at the first determined location from the resource availability information, the first necessary inspection or the first necessary treatment specified in the inspection treatment database, and
  a fourth region upon which an activation of the fourth region reserves, at the second determined location from the resource availability information, the second necessary inspection or the second necessary treatment specified in the inspection treatment database; and
perform in the pop-up menu a cancellation for the at least one of the necessary inspection or the necessary treatment by activating the third region or the fourth region.

2. The inspection information display device according to claim 1, wherein the processor is further configured to display a minified picture of the medical image on the display unit.

3. The inspection information display device according to claim 1, wherein in the inspection treatment database, each human portion is associated with multiple symptoms, and multiple necessary inspections or multiple necessary treatments.

4. The inspection information display device according to claim 1, wherein determine the at least one of a necessary inspection or a necessary treatment to confirm the analysis result by referring to the inspection treatment database comprising:
  determine at least one of a necessary inspection or a necessary treatment to confirm the analysis result by referring to the inspection treatment database at least by:
    determine a first human portion or a second human portion based on the analysis result;
    determine a first symptom or a second symptom in a case of the first human portion;
    determine a third symptom or a fourth symptom in a case of the second human portion;
    determine a first set of medical inspections and treatments as the necessary inspection or a necessary treatment in a case of the first symptom;
    determine a second set of medical inspections and treatments as the necessary inspection or a necessary treatment in a case of the second symptom;
    determine a third set of medical inspections and treatments as the necessary inspection or a necessary treatment in a case of the third symptom; and
    determine a fourth set of medical inspections and treatments as the necessary inspection or a necessary treatment in a case of the fourth symptom.

5. An inspection information display method comprising:
displaying an analysis result obtained by analyzing data related to a patient and inspection information related to the data on a display unit;
deciding at least one of a necessary inspection or a necessary treatment to confirm the analysis result by referring to an inspection treatment database which includes multiple entries with each of the multiple entries associates among a human portion, a symptom, and a necessary inspection or a necessary treatment and by selecting the necessary inspection or the necessary treatment according to a corresponding human portion and symptom;
acquiring the resource availability information to determine at least a location for executing the at least one of the selected necessary inspection or the necessary treatment;
detecting, as shown on the display unit, a cursor being on the analysis result or on a degree of urgency field;
displaying in a pop-up menu that indicating resource availability information, the selected at least one of the necessary inspection or the necessary treatment, and the determined location for performing the selected at least one of the necessary inspection or the necessary treatment in response to detecting the cursor being on the analysis result or on the degree of urgency field; and, wherein the pop-up menu as the result of detecting the cursor being on the analysis result further comprises
  a first region upon which an activation of the first region reserves, at a first determined location from the resource availability information, a first necessary inspection or a first necessary treatment specified in the inspection treatment database, and
  a second region upon which an activation of the second region reserves, at a second determined location from the resource availability information, a second necessary inspection or a second necessary treatment specified in the inspection treatment database;
performing in the pop-up menu a reservation for the at least one of the necessary inspection or the necessary treatment based on the resource availability information by activating the first region or the second region;
displaying in a pop-up menu that indicating resource availability information, the selected at least one of the necessary inspection or the necessary treatment, and the determined location for performing the selected at least one of the necessary inspection or the necessary treatment in response to detecting the cursor being on the degree of urgency field; wherein the pop-up menu as the result of detecting the cursor being on the degree of urgency field further comprises
  a third region upon which an activation of the third region cancels, at the first determined location from the resource availability information, the first necessary inspection or the first necessary treatment specified in the inspection treatment database, and
  a fourth region upon which an activation of the fourth region reserves, at the second determined location from the resource availability information, the second necessary inspection or the second necessary treatment specified in the inspection treatment database; and performing in the pop-up menu a cancellation for the at least one of the necessary inspection or the necessary treatment by activating the third region or the fourth region.

6. A non-transitory computer readable recording medium storing an inspection information display program causing a computer to execute:

a procedure of displaying an analysis result obtained by analyzing data related to a patient and inspection information related to the data on a display unit;

a procedure of deciding at least one of a necessary inspection or a necessary treatment to confirm the analysis result by referring to the inspection treatment database which includes multiple entries with each of the multiple entries associates among a human portion, a symptom, and a necessary inspection or a necessary treatment and by selecting the necessary inspection or the necessary treatment according to a corresponding human portion and symptom;

a procedure of acquiring the resource availability information to determine at least a location for executing the at least one of the selected necessary inspection or the necessary treatment;

a procedure of detecting, as shown on the display unit, a cursor being on the analysis result or on a degree of urgency field;

a procedure of displaying in a pop-up menu that indicating resource availability information, the selected at least one of the necessary inspection or the necessary treatment and the determined location for performing the selected at least one of the necessary inspection or the necessary treatment, in response to detecting the cursor being on the analysis result, wherein the pop-up menu as the result of detecting the cursor being on the analysis result further comprises a first region upon which an activation of the first region reserves, at a first determined location from the resource availability information, a first necessary inspection or a first necessary treatment specified in the inspection treatment database, and a second region upon which an activation of the second region reserves, at a second determined location from the resource availability information, a second necessary inspection or a second necessary treatment specified in the inspection treatment database;

a procedure of performing in the pop-up menu a reservation for the at least one of the necessary inspection or the necessary treatment based on the resource availability information by activating the first region or the second region;

a procedure of displaying in a pop-up menu that indicating resource availability information, the selected at least one of the necessary inspection or the necessary treatment, and the determined location for performing the selected at least one of the necessary inspection or the necessary treatment in response to detecting the cursor being on the degree of urgency field; wherein the pop-up menu as the result of detecting the cursor being on the degree of urgency field further comprises a third region upon which an activation of the third region cancels, at the first determined location from the resource availability information, the first necessary inspection or the first necessary treatment specified in the inspection treatment database, and a fourth region upon which an activation of the fourth region reserves, at the second determined location from the resource availability information, the second necessary inspection or the second necessary treatment specified in the inspection treatment database; and a procedure of performing in the pop-up menu a cancellation for the at least one of the necessary inspection or the necessary treatment by activating the third region or the fourth region.

7. An inspection information display device comprises:

a memory that stores a command to be executed by a computer; and a processor configured to display an analysis result obtained by analyzing data related to a patient and inspection information related to the data on a display;

decide at least one of a necessary inspection or a necessary treatment to confirm the analysis result by referring to the inspection treatment database which includes multiple entries with each of the multiple entries associates among a human portion, a symptom, and a necessary inspection or a necessary treatments and by selecting the necessary inspection or the necessary treatment according to a corresponding human portion and symptom;

acquire the resource availability information to determine at least a location for executing the at least one of the selected necessary inspection or the necessary treatment;

detect, as shown on the display unit, a cursor being on the analysis result or on a degree of urgency field;

display in a pop-up menu that indicating resource availability information, the selected at least one of the necessary inspection or the necessary treatment, and the determined location for performing the selected at least one of the necessary inspection or the necessary treatment in response to detecting the cursor being on the analysis result, wherein the pop-up menu as the result of detecting the cursor being on the analysis result further comprises a first region upon which an activation of the first region reserves, at a first determined location from the resource availability information, a first necessary inspection or a first necessary treatment specified in the inspection treatment database, and a second region upon which an activation of the second region reserves, at a second determined location from the resource availability information, a second necessary inspection or a second necessary treatment specified in the inspection treatment database;

perform in the pop-up menu a reservation for the at least one of the necessary inspection or the necessary treatment based on the resource availability information by activating the first region or the second region;

display in a pop-up menu that indicating resource availability information, the selected at least one of the necessary inspection or the necessary treatment, and the determined location for performing the selected at least one of the necessary inspection or the necessary treatment in response to detecting the cursor being on the degree of urgency field; wherein the pop-up menu as the result of detecting the cursor being on the degree of urgency field further comprises a third region upon which an activation of the third region cancels, at the first determined location from the resource availability information, the first necessary inspection or the first necessary treatment specified in the inspection treatment database, and a fourth region upon which an activation of the fourth region reserves, at the second determined location from the resource availability information, the second necessary inspection or the second necessary treatment specified in the inspection treatment database; and perform in the pop-up menu a cancellation for the at least one of the necessary inspection or the necessary treatment by activating the third region or the fourth region.

\* \* \* \* \*